United States Patent [19]

Burnouf-Radosevich et al.

[11] Patent Number: 5,260,420

[45] Date of Patent: Nov. 9, 1993

[54] CONCENTRATE OF THROMBIN COAGULABLE PROTEINS, THE METHOD OF OBTAINING SAME AND THERAPEUTICAL USE THEREOF

[75] Inventors: Miryana Burnouf-Radosevich; Thierry Burnouf, both of Wavrin, France

[73] Assignee: Centre Regional de Transfusion Sanguine de Lille, Lille, France

[21] Appl. No.: 873,106

[22] Filed: Apr. 24, 1992

Related U.S. Application Data

[60] Division of Ser. No. 776,671, Oct. 9, 1991, abandoned, which is a continuation of Ser. No. 226,364, Jul. 29, 1988, abandoned.

[30] Foreign Application Priority Data

Jul. 30, 1987 [FR] France .................. 87 10798

[51] Int. Cl.$^5$ .................. A61K 35/16; A61K 9/14
[52] U.S. Cl. .................. 530/382; 530/381
[58] Field of Search .................. 530/381, 382

[56] References Cited

U.S. PATENT DOCUMENTS

| | | | |
|---|---|---|---|
| 4,362,567 | 12/1982 | Schwarz et al. | 530/382 |
| 4,374,061 | 2/1983 | Bing | 530/380 |
| 4,377,572 | 3/1983 | Schwarz et al. | 514/21 |
| 4,427,650 | 1/1984 | Stroetmann | 514/21 |
| 4,568,545 | 4/1986 | Mihara et al. | 424/94.64 |
| 4,613,501 | 9/1986 | Horowitz | 530/382 |
| 4,627,879 | 12/1986 | Rose et al. | 514/2 |
| 4,640,834 | 2/1987 | Eibl et al. | 424/94.2 |

FOREIGN PATENT DOCUMENTS

2041942 9/1980 United Kingdom .

OTHER PUBLICATIONS

Quinn et al. (1983), Abstract, J. Pharm. Sci. 72, 1472.
Biological Abstracts, vol. 77, No. 7, 1984, resume No. 49207, Philadelphia, U.S., M. G. Ikossi-O'Connor et al: "The Role of Fibrin Adhesive in Vascular Surgery".

*Primary Examiner*—Howard E. Schain
*Assistant Examiner*—P. Lynn Touzeau
*Attorney, Agent, or Firm*—Birch, Stewart, Kolasch & Birch

[57] ABSTRACT

The invention provides a thrombin coagulable protein concentrate, the preparation thereof and the therapeutic use thereof. This concentrate has a fibrinogen content greater than 70% and a sufficient amount of endogenous Factor XIII. It may be solubilized at ambient temperature. Its preparation comprises at least one cold precipitation step with dilute ethanol and uses total plasma as a starting product. The concentrate of the invention makes it possible more particularly to obtain an injectable fibrinogen and a biological glue of high quality.

6 Claims, 1 Drawing Sheet

| Proteins | % |
|---|---|
| γ | 95,6 |
| α2.β | 4,4 |

| | |
|---|---|
| γ | 61,3 |
| α2.β | 10,8 |
| Albumin | 26,8 |

| | |
|---|---|
| γ | 80,6 |
| α2.β | 2,9 |
| Albumin | 16,5 |

| | |
|---|---|
| γ | 48,8 |
| α2.β | 14,8 |
| Albumin | 34,3 |

CONCENTRATE OF THROMBIN COAGULABLE PROTEINS, THE METHOD OF OBTAINING SAME AND THERAPEUTICAL USE THEREOF

This application is a divisional of copending application Ser. No. 07/776,671, filed on Oct. 9, 1991, now abandoned, which is a Rule 62 continuation of Ser. No. 07/226,364, filed Jul. 29, 1988, the entire contents of which are hereby incorporated by reference now abandoned.

BACKGROUND OF THE INVENTION

The present invention relates to a concentrate of thrombin in coagulable proteins, a method of obtaining the same from total plasma and a use thereof for therapeutic purposes.

This type of concentrate may be used for obtaining, by redissolution, an injectable fibrinogen or a biological glue.

As is known, injections of fibrinogen make it possible to treat hypofibrinogenesis or constitutional afibrinogenesis conditions, with or without hemorrhages, and also the acute defibrination syndromes with serious hemorrhages, in association with etiological treatment, heparinotherapy or antifibrinolyties.

On the other hand, biological glues make it possible to give efficient help during certain clinical episodes such as skin grafts, nerve or artery sutures, rapid cicatrization or any use where a hemostatic and/or bacteriostatic and/or aesthetic effect is sought. In fact, fibrinogen, a major constituent in such a concentrate, undergoes enzymatic degradation in contact with thrombin activated by calcium ions. After elimination of the fibrinopeptides A and B, the fibrin monomers polymerize and spontaneously generate soluble fibrin. The presence of Factor XIII in this type of product contributes to stabilizing the fibrin by covalent bonds by making it insoluble, i.e. resistant to solvent (e.g., urea). The fibrin thus stabilized, in addition to its coagulant role, is more resistant to fibrinolysis and to mechanical tractia.

For these different therapeutic uses, it is necessary to have available a product of plasmatic origin with good solubility and stable under the conditions of use. In so far as biological glues are concerned, it is further necessary for them to have, after being placed in contact with the calcic thrombin, a high adhesive power and high elasticity.

The fact of obtaining such characteristics is directly related to the nature of the product and so to the method of purification thereof from plasma. It is then useful to have a preparation technique readily usable on an industrial scale but which is also sufficiently gentle so as not to impair the biochemical qualities of the product for the desired use by clinicians.

Glues containing fibrinogen and Factor XIII are already known particularly from French patents No. 2,448,900 and 2,448,901. These products are obtained from plasma cryoprecipitate by treating with a buffer solution containing plasminogen inhibitor-activator or plasmin inhibitor, which is present in the glue in the lyophilized state.

These products have interesting characteristics. However, these products are obtained using fairly complex fibrinogen production methods which require, so as to have a final satisfactory mixture, the exogenous addition of other plasmatic proteins such as Factor XIII. Moreover, during production, inhibitors must be added such as protease inhibitors of animal origin such as bovine aprotinin.

Furthermore, the known protein concentrates, in particular those used as glues, do not solubilize in an aqueous medium at ambient temperature and may even be difficult to solubilize at 37° C., making it necessary to add to the lyophilization vial of the product a magnetized bar and provide a magnetic agitator used for accelerating the solubilization.

It would then be quite beneficial to have available a simple method of producing biological glue so as to obtain without exogenous addition of proteins, a protein mixture corresponding to the desired qualities for such a product. In particular, for the use as glue, the concentrate obtained should have satisfactory fibrinogen, Factor XIII and fibronectin content.

The method in question must also be readily adaptable to modifications for introducing a viral inactivation step. The resultant product should solubilize in less than 10 minutes at the temperature of use (generally 18° to 20° C.) without requiring special tools. The product should also be stable for several hours so as to facilitate use and guarantee the clinical efficiency thereof.

SUMMARY OF THE INVENTION

The Applicant has perfected a simple method for preparing a thrombin coagulable protein concentrate, containing, through the simple fractionation used, more than 70% of coagulable fibrinogen with respect to the whole of the proteins present, and a satisfactory amount of endogenous -Factor XIII by a technique using a plasmatic fraction available in all the fractionation centers.

DETAILED DESCRIPTION OF THE INVENTION

The invention relates then to a thrombin coagulable protein concentrate obtained by precipitation and treatment of human or animal plasma with ethanol, which advantageously contains more than 70% by weight of coagulable fibrinogen with respect to the total proteins and endogenous Factor XIII.

This concentrate, contrary to those known at present, solubilizes rapidly in an aqueous medium at ambient temperature, namely in less than 10 minutes for a protein content which may reach 150 g/l. Furthermore, it remains stable after reconstitution for at least 24 hours when it is kept at a temperature, for example, between 4° and 37° C.

This concentrate advantageously contains, per gram of proteins, at least 0.10 UI of endogenous Factor XIII.

It further contains a balanced amount of fibronectin, in particular between 0.03 and 0.10 g/gram of proteins.

For use as injectable fibrinogen, the concentrate is formulated and conditioned so as to obtain after reconstitution by resolubilization, a total protein content of the order of 17 to 29 g/l. For use as biological glue, this content will be between about 100 and 120 g/l.

The concentrate of the invention is obtained by a method comprising a step for precipitation with dilute ethanol, with a pH close to neutrality and at a low temperature, of a total plasma not subjected to r-ryoprecipitation.

The operating conditions of the method are adjusted so as to obtain a precipitate which is little denatured, thus avoiding the degradations to which the proteins would be subjected if the precipitation step took place under conventional industrial plasma processing conditions. Thus, apart from the precautions taken, particularly in so far as the ethanol concentration and the temperature are concerned, the plasma is preferably processed in small sized containers (e.g. of 10 liters) provided with magnetized bars. The plasma is then placed in contact with the low concentration ethanol, e.g. from 8 to 12%, for a time which may extend to several days and isoin any case, greater than 24 hours. The supernatant is then decanted and is available for the preparation of other derivatives.

The precipitate obtained, after centrifugation, is washed with ethanol, still at a low temperature, i.e. between 0° and 6° C., and with an 8 to 12% degree of alcohol, preferably 10% and the whole is centrifuged.

The precipitate is then resolubilized in a Tris/citrate buffer, possibly concentrated, filtered and preferably lyophilized before subsequent treatment. If required, it may be processed directly, i.e. in the non lyophilized state.

The subsequent treatment carried out to obtain a protein concentrate in accordance with the invention may be provided in two distinct variants.

In a first variant, the lyophilizate or the corresponding fresh paste is resolublized in water or Tris/citrate buffer advantageously containing lysine and the solution is treated with warm dilute ethanol.

In accordance with this variant; the fibrinogen lyophilizate or the corresponding fresh paste, is resolubilized at a protein content of the order of 50 g/l and subjected to treatment with 8 to 12% ethanol, at a temperature between 30° and 40° C., preferably at 3.5° C. and for a time of about an hour and a half. This step, carried out preferably in the presence of lysine, contributes to correct solubilization of the lyophilized biological glue, while providing increased safety with respect to the inactivation of possible pathogenic viruses, including the AIDS virus.

The amount of lysine used makes it possible, for example, to have a concentration of 0.1 to 0.2 g/gram of proteins in the ready for use product.

The ethanol is eliminated by ultra- or disfiltration against a buffer preferably containing an amount of lysine corresponding to the desired amount in the ready to use product, but advantageously without citrate so that the concentration of this compound in the final product is the lowest possible considering its apparently harmful action in the coagulation phenomenon. Tris/NaCl/lysine buffer is for example used.

The product is then filtered in a sterile atmosphere, dispensed in its vial of use and lyophilized.

According to the second variant, the lyophilizate, or the corresponding fresh paste, after resolubilization is subjected to a viral inactivation step, e.g. to treatment with solvent and detergent. The residues of this treatment are then eliminated preferably by a cold precipitation step using dilute ethanol.

In this variant, the fibrinogen lyophilizate, or the corresponding fresh paste, is then resolubilized with a protein content of about 20 g/l. It is then subjected to a viral inactivation treatment for example to a treatment with solvent and detergent.

This step, carried out advantageously at a temperature greater than 24° C. and for a time greater than 6 hours, provides increased safety with respect to the inactivation of possible pathogenic viruses including the AIDS virus and the hepatitis virus. It is preferably carried out in the presence of lysine at a concentration corresponding to a lysine content of the ready to use product of about 0.1 to 0.2 g/gram of proteins.

The elimination of the viral inactivation agents conjointly with the increase in the purity of the protein concentrate is provided by reprecipitation of the proteins at low temperature using 8 to 12% ethanol. After centrifugation, the viral inactivation agents and the contaminating proteins such as albumin are in fact eliminated in the supernatant. If required, the precipitate can again be placed in contact with the ethanol solution so as to provide better elimination of the viral inactivation agents.

The precipitate is again solubilized in a Tris/citrate/lysine buffer solution then ultra-filtered and disfiltered before sterilizing filtration and distribution. The purpose of the ultrafiltration is to eliminate the ethanol as well as the citrate but also to maintain a constant lysine content of 0.1 to 0.2 g per g of proteins.

When the concentrate of the invention serves as a biological glue, the reconstitution of the glue before use of the product is provided by means of an aqueous aprotinin solution at the rate of 10000 UI/ml, the resultant solution being mixed with calcic thrombin at the rate of 500 UI/ml.

The product is used either in liquid form dispensed by means of a double needle system (reconstituted biological glue on the one hand and calcic thrombin on the other hand) or in dry form (use as a powder) or by a spray system.

The following examples illustrate the invention without limiting the scope thereof.

EXAMPLE 1

A. Preparation of the Protein Concentrate

The plasma used is obtained by the centrifugation of blood and frozen to −35° C. within six hours following blood collection. For preparing the concentrate, it is thawed to 37° C. Then, it is subjected to precipitation with 10% ethanol with a pH of 7.2, a protein content of 52 g/l and a temperature of 4° C. The mixture is agitated for 30 minutes then allowed to settle for a minimum time of 24 hours at 4° C.

The ethanol supernatant is eliminated by centrifugation and the precipitate, enriched more especially in fibrinogen and Factor XIII, is recovered. The latter is thoroughly washed with a 10% solution of ethanol precooled to +4° C. then centrifuged again.

The precipitate is then resolubilized using a Tris/citrate buffer solution, then concentrated to 15-20 g/l of proteins, filtered and lyophilized, if required.

The resultant product is then put back into suspension at a rate of 50 g/l of proteins using a 3 g/l lysine solution (corresponding to a lysin content of the final product of 0.1 to 0.2 g/gram of proteins), then subjected to a second treatment with 10% ethanol, for an hour and a half at 35° C.

After disfiltration for eliminating the citrate and the ethanol and bringing the protein content to the adequate value, e.g. 35 g/l, the concentrate is filtered, dispensed in a sterile atmosphere and lyophilized in the final vial for subsequent use as a 0. 5, 1, 2 or 5 ml solution, for example, at the time of use.

B. Biochemical Analysis of the Protein Concentrate

The protein composition of the product is the following (expressed per gram of proteins):

| | |
|---|---|
| Fibrinogen | 0.70–0.75 g |
| Endogenous Factor XIII | 0.10–0.25 UI |
| Fibronectin | 0.05–0.10 g |

EXAMPLE 2

A. Preparation of the Protein Concentrate

The plasma used is obtained by the centrifugation of blood and frozen to −35° C. within the six hours following blood collection. For preparing the concentrate, it is thawed to 37° C. Then it is subjected to precipitation with 10% ethanol with a pH of 7.2, a protein content of 52 g/l and a temperature of 4° C. The mixture is agitated for 30 minutes then allowed to settle for a minimum time of 24 hours at 4° C.

The ethanol supernatant is eliminated by centrifugation and the precipitate, enriched more especially in fibrinogen and Factor XIII, is recovered. The latter is thoroughly washed with a 10% solution of ethanol precooled to +4° C. then again centrifuged.

The precipitate is then put back into solution using a Tris/citrate buffer solution, then concentrated to 15–20 g/l of proteins, filtered and lyophilized if required.

The resultant product is then put back into suspension at a content of about 20 g/l of proteins using a lysine solution corresponding to a lysine content of the final product of 0.1 to 0.2 g/gram of proteins then is subjected to treatment by solvent and detergent with 0.3% of TNBP and 1% of Tween 80 for a time greater than 6 hours and at a temperature greater than 24° C.

The solution is then subjected to alcohol precipitation using 10% ethanol, at 4° C. and is left to decant for 10 hours or so.

After centrifugation and elimination of the supernatant (which may contain viral inactivation agents), the precipitate is recovered then solubilized using a Tris/citrate buffer containing lysine in an amount corresponding to 0.1–0.2 gram of lysine per gram of proteins.

After disfiltration for adjusting the ionic strength, eliminating the citrate and the ethanol (but keeping the lysine) and bringing the protein content to an adequate value, e.g. about 35 g/l, the concentrate is filtered, dispensed i-n a sterile atmosphere and lyophilized in the final vial for subsequent use as a 0.5, 1, 2 or 5 ml solution at the time of use.

B. Biochemical Analysis of the Protein Concentrate

The protein composition of the product is the following (expressed per gram of proteins):

| | |
|---|---|
| Fibrinogen | 0.90–0.95 g |
| Endogenous Factor XIII | 0.15–0.30 UI |
| Fibronectin | 0.03–0.06 g |

BRIEF DESCRIPTION OF THE DRAWING

The single accompanying figure shows the results of analysis by electrophoresis obtained respectively for this concentrate (curve 1a) and for commercial concentrates used as biological glues (curves 1b to 1d).

The appreciably greater purity in constituents of zone γ (fibrinogen) of the product of the invention is clear from these curves.

Figure 1A:
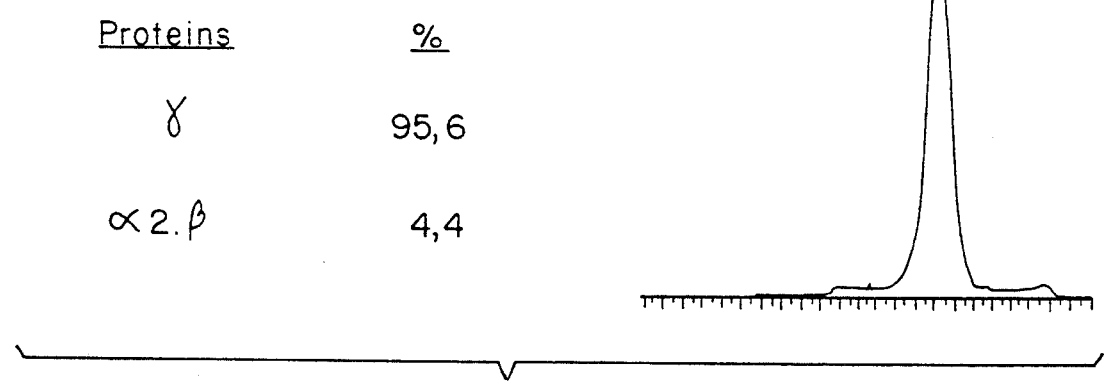
Figure 1B:
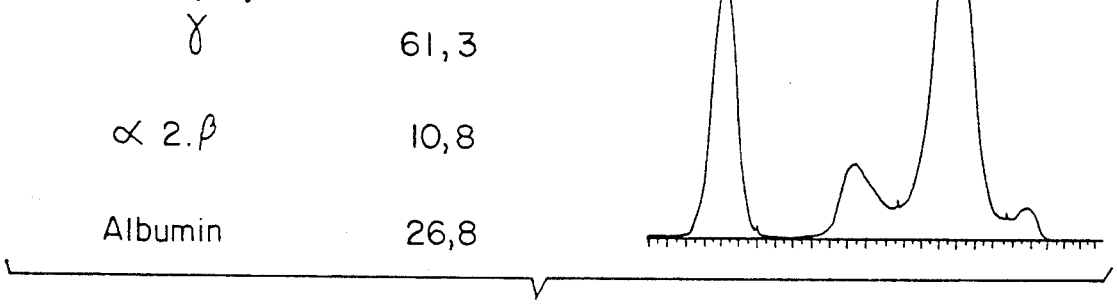
Figure 1C:
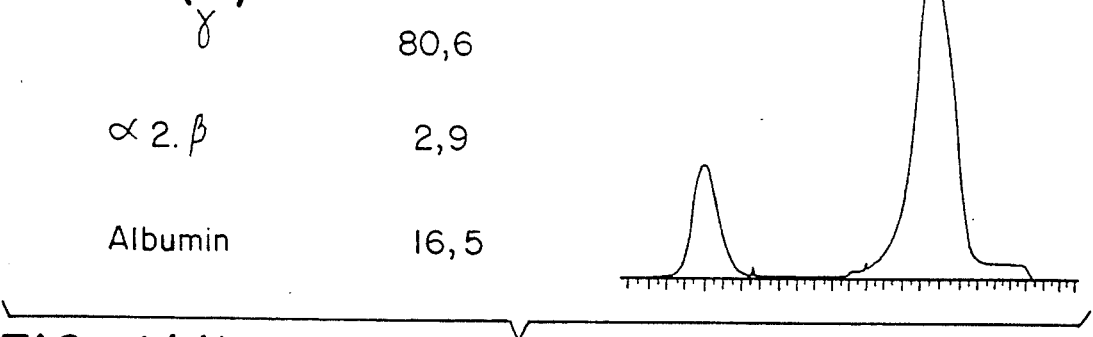
Figure 1D:
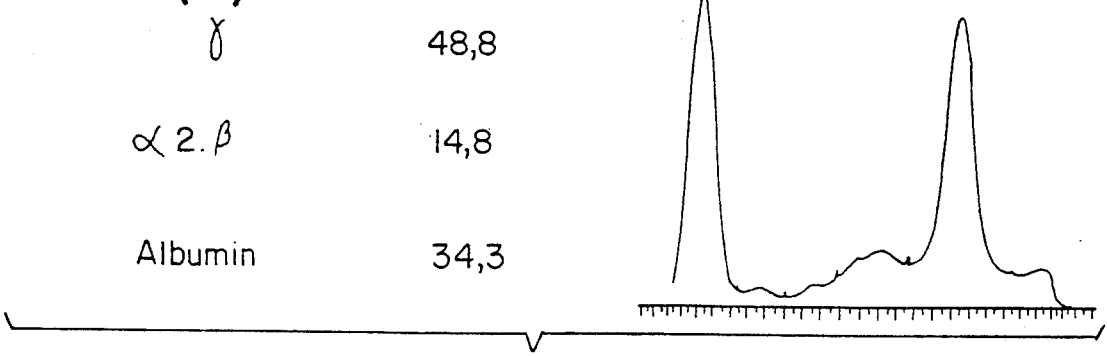

As mentioned above, the concentrate of the invention has excellent solubilization and stability characteristics. In fact, its solubilization time is less than 10 mins, even 5 mins, not only at 37° C. but also at 20° C., without special apparatus, by a simple manual rotational movement.

Furthermore, no destabilization is observed of the reconstituted product kept at 4°, 20° or 37° C. for a period of 24 hours.

In so far as a biological glue of the invention is concerned, it can be seen that it has excellent characteristics for use as such. In fact, its adhesive power is greater than 100 g/cm$^2$ expressed by the test of sticking skin strips on animals, a value greater than those obtained with other glues prepared from a cryoprecipitate. This adhesive power is maintained at 90% of its value after reconstitution of the biological glue and conservation for 24 hours at 4° C. or at 20° C. Moreover, no exudation is observed during mixing of the protein concentrate with the calcic thrombin. Clinical tests carried out have shown the great adaptability of this glue to the constraints of use: need of rapid solubilization, stability at the temperatures of operating theaters, possibility of delay in use.

The uses of the glue of the invention follow from its properties: its adhesive and hemostatic power make it a precious adjuvant in surgical operations during which it ensures a gain in operating time. Furthermore, its bacteriostatic power reinforces and accelerates the cicatrization of wounds and sutures.

It uses thus apply to very varied surgical fields
Plastic surgery and microsurgery: skin grafts of burns, gluing of strips, lifting, blepharoplasty.
Neurosurgery: plastic surgery and dura mater suture, tumoral exeresis hemostasis, venous sinus hemostasis.
Cardiovascular surgery: sealing of sutures of vascular prostheses, aortic dissection, aneurysm.
General and abdominal surgery: sticking of visceral tears (splenic, renal, hepatic ... or hepatic biopsy, digestive anastomoses, fistulas, hemostasis of the operative cavities.
Bone surgery: cortical bonding, suture of the tendon,, osteomyelitis seat bonding.
Stomatology: hemostasis of dental extraction seats in patients with high hemorrhagic risk (hemophiliaes).
Otorhinolaryngology: tympanic wound repair, tonsillectomy.

The glue of the invention may be prepared from human or animal plasma and thus can be advantageously used for human or veterinary treatment.

In so far as an injectable fibrinogen of the invention is concerned, it is observed that it also has excellent characteristics of use and that its balanced composition makes it a precious therapeutic agent for the treatment of hypo- or afibrinogenesis conditions and for the syndrome of acute defibrination.

For the treatment of constitutional deficiencies, the usual dose is 1 to 4 g depending on the weight of the patient, considering that the half life of fibrinogen is 3 to 4 days and the plasmatic content required to have a sufficient hemostasis is about 1 g/l.

In acute defibrination conditions, the doses vary from 2 to 10 g depending on the circumstances.

The therapeutic products of the invention may be prepared from human or animal plasma and thus find their interest not only in human but also in veterinary medicine.

We claim:

1. A method for preparing a lyophilized plasma-derived protein concentrate comprising Factor XIII, fibronectin and more than 70% fibrinogen, said concentrate being clottable in the presence of thrombin and calcium to form biological glue, which comprises the steps of:

precipitating a non-cryoprecipitated total plasma with cold dilute ethanol to obtain a first precipitate;

washing said first precipitate with cold dilute ethanol to obtain a washed first precipitate;

resolubilizing said washed first precipitate in tris/citrate buffer in the presence of lysine to obtain a first solution;

precipitating said first solution with dilute ethanol to obtain a second precipitate;

resolubilizing said second precipitate in tris/citrate buffer in the presence of lysine to obtain a second solution;

diafiltrating and lyophilizing said second solution to obtain said lyophilized plasma-derived protein concentrate.

2. The method according to claim 1, wherein said non-cryoprecipitated total plasma is precipitated by contacting with 10% ethanol, at a temperature of 4° C., for about 12 hours.

3. The method according to claim 1, wherein said lysine is present in an amount corresponding to a content in the final product of 0.1 to 0.2 g per gram of protein.

4. The method according to claim 1, wherein said first solution is precipitated by contacting with 10% ethanol at a temperature between 30° and 40° C., for about 90 minutes.

5. The method according to claim 1, wherein said first solution is subjected to a viral inactivation treatment.

6. The method according to claim 5, wherein said viral inactivation treatment comprises treatment with a solvent and detergent.

* * * * *